United States Patent [19]

Hall et al.

[11] 4,150,140
[45] Apr. 17, 1979

[54] BENZOTHIAZOLYL OXANIC ACIDS, ESTERS AND SALTS

[75] Inventors: Charles M. Hall; John B. Wright, both of Kalamazoo, Mich.

[73] Assignee: The Upjohn Company, Kalamazoo, Mich.

[21] Appl. No.: 753,717

[22] Filed: Dec. 23, 1976

[51] Int. Cl.² .................. C07D 277/82; A61K 31/425
[52] U.S. Cl. ..................................... 424/270; 260/305
[58] Field of Search ......................... 260/305; 424/270

[56] References Cited

U.S. PATENT DOCUMENTS 3,538,089 11/1970 Schmidt et al. ...................... 260/243
3,966,965 6/1976 Sellstedt et al. ..................... 424/309

OTHER PUBLICATIONS

Petyunin et al. - C. A. 60, 10591 (1964).

Primary Examiner—Raymond V. Rush
Attorney, Agent, or Firm—Martin B. Barancik

[57] ABSTRACT

Compounds of the formula

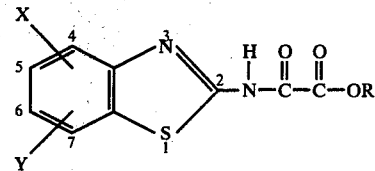

wherein X and Y are the same or different and are hydrogen, fluoro, chloro, bromo, alkyl of one to six carbon atoms, inclusive, alkoxy of one to six carbon atoms, inclusive, nitro, cyano, amino, trifluoromethyl,

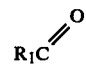

wherein $R_1$ is alkyl of one to six carbon atoms, inclusive,

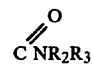

wherein $R_2$ and $R_3$ are the same or different and are hydrogen or alkyl of one to three carbon atoms inclusive, or $CO_2Q$ where Q is alkyl of one to six carbon atoms, inclusive, hydrogen or a physiologically acceptable metal or amine cation; and R is hydrogen, alkyl of one to eight carbon atoms, inclusive, —$CH_2)_m$ phenyl wherein m is 0, 1 or 2 or $(CH_2)_nNR_4R_5$ wherein n is 1 or 2, and $R_4$ and $R_5$ are the same or different and are alkyl of one to three carbon atoms, inclusive, and a physiologically acceptable metal or amine cation; and physiologically acceptable acid addition salts thereof are formulated into pharmaceutical compositions suitable for oral, parenteral or inhalation administration which are used as prophylactic inhibitors of allergic manifestations in sensitized mammals.

25 Claims, No Drawings

BENZOTHIAZOLYL OXANIC ACIDS, ESTERS AND SALTS

BRIEF SUMMARY OF THE INVENTION

It has now been discovered that novel compounds of Formula I are useful in the prophylactic treatment of sensitized mammals for allergy and anaphylactoid reactions of a reagin or non-reagin mediated nature. The compounds are formulated with pharmaceutical carriers for oral, parenteral, or inhalation means of administration.

DETAILED DESCRIPTION OF THE INVENTION

In accordance with this invention there are provided compounds, hereafter referred to as Group A, represented by Formula I

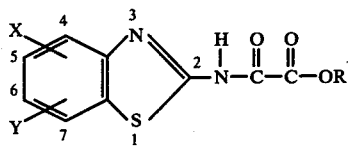

Formula 1 wherein X and Y are the same or different and are hydrogen, fluoro, chloro, bromo, alkyl of one to six carbon atoms, alkoxy of one to six carbon atoms, inclusive, nitro, cyano, amino, trifluoromethyl,

wherein $R_1$ is alkyl of one to six carbon atoms, inclusive,

wherein $R_2$ and $R_3$ are the same or different and are hydrogen or alkyl of one to three carbon atoms, inclusive, or $CO_2Q$ where Q is alkyl of one to six carbon atoms, inclusive, hydrogen or a physiologically acceptable metal or amine cation; and R is hydrogen, alkyl of one to eight carbon atoms, inclusive, —$CH_2)_m$ phenyl wherein m is 0, 1 or 2 or $(CH_2)_nNR_4R_5$ wherein n is 1 or 2, and $R_4$ and $R_5$ are the same or different and are alkyl of one to three carbon atoms, inclusive, and a physiologically acceptable metal or amine cation; and physiologically acceptable acid addition salts thereof.

A further group of compounds, hereafter referred to as Group B, are the compounds of Group A where X and Y are the same or different and are hydrogen, fluoro, chloro, bromo, alkyl of one to four carbon atoms, inclusive, alkoxy of one to four carbon atoms, inclusive, cyano, amino, nitro,

wherein $R_1$ is alkyl of one to four carbon atoms, inclusive, trifluoromethyl or $CO_2Q$ where Q is alkyl of one to four carbon atoms, inclusive, hydrogen or a physiologically acceptable metal or amine cation.

Another group of compounds, hereafter referred to as Group C are those compounds of Group B wherein X and Y are the same or different and are hydrogen, fluoro, chloro, alkyl of one to three carbon atoms, inclusive, alkoxy of one to three carbon atoms, inclusive, cyano, amino, nitro,

wherein $R_1$ is alkyl of one to three carbon atoms, inclusive, trifluoromethyl or $CO_2Q$ where Q is alkyl of one to three carbon atoms, inclusive, hydrogen or a physiologically acceptable metal or amine cation.

A still further group of compounds, hereafter referred to as Group D, are those compounds of Group C wherein X is hydrogen.

Another group of compounds, hereafter referred to as Group E, are those compounds of Group D wherein Y is at the six position.

A further group of compounds, hereafter referred to as Group F are those compounds of Group A wherein R is hydrogen or a physiologically acceptable metal or amine cation.

Another group of compounds, hereafter referred to as Group G are those compounds of Group A wherein R is $(CH_2)_nNR_4R_5$ wherein n is 1 or 2.

A further group of compounds, hereafter referred to as Group H, are those compounds of Group A wherein R is alkyl of one to eight carbon atoms, inclusive, or —$CH_2)_m$ phenyl wherein m is 0, 1 or 2.

Another group of compounds, hereafter referred to as Group I, are those compounds of Group H wherein R is alkyl of one to six caborn atoms, inclusive, or —$CH_2)_m$ phenyl wherein m is 0, 1 or 2.

A further group of compounds, hereafter referred to as Group J, are those compounds of Group I wherein R is alkyl of one to four carbon atoms, inclusive.

Another group of compounds are those of Group B wherein R is defined as in Group I.

A further group of compounds are those of Group C wherein R is defined as in Group I.

Another group of compounds are those of Group D wherein R is defined as in Group I.

A final group of compounds are those of Group E wherein R is defined as in Group I.

Pharmaceutical compositions and methods of using these compositions for prophylactically treating allergy of a reagin mediated nature utilizing each of the above groups of compounds is within the concept of the invention.

As employed in the above disclosure and throughout the specification and claims, the phrase "alkyl of one to eight carbon atoms, inclusive" includes methyl, ethyl, propyl, butyl, pentyl, hexyl, heptyl, octyl and isomers thereof. Illustrative examples of isomers are isopropyl, tert-butyl, neopentyl, 2,2-dimethylbutyl, 2-methylhexyl and 2,2,4-trimethylpentyl. Alkyl of a smaller number of carbon atoms has a similar scoping.

The phrase "physiologically acceptable amine salt" refers to amines which are accepted by mammals in an essentially non-toxic manner when administered to mammals in conjunction with the acid moiety of the invention. Illustrative of the amines are those derived from primary, secondary or tertiary amines. Examples of suitable amines are methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, adamantylamines, and like aliphatic, cycloaliphatic, and araliphatic amines containing up to and including about eighteen carbon atoms as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-1-ethyl-1,3-propanediol, 2-amino-2-methyl-1-propanol, tris(hydroxymethyl)aminomethane, N-phenylethanolamine, N-(p-tert-amylphenyl)diethanolamine, galactamine, N-methylglucamine, N-methylglucosamine, ephedrine, phenylephrine, epinephrine, procaine, and the like. Also included within the amine scope are quaternary amines such as ammonium, tetramethylammonium, tetraethylammonium, benzyltrimethylammonium, phenyltriethylammonium, and the like.

The term "physiologically acceptable metal" includes alkali metals such as sodium and potassium, alkaline earth metals such as calcium and magnesium, and other acceptable metals such as aluminum.

The phrase "physiologically acceptable acid addition salts thereof" refers to compounds wherein a nitrogen is sufficiently basic so as to interact in the presence of an essentially non-toxic acid such as hydrochloric, sulfuric, nitric, lauric or cyclohexanesulfamic and the like. Examples of such compounds of Formula I are compounds wherein X and/or Y is amino and compounds wherein R is $(CH_2)_n$—$NR_4R_5$.

The compounds of this invention are prepared by standard methods known in the art. An X and/or Y substituted 2-aminobenzothiazole is reacted with an alkyl oxalyl halide, preferably ethyl oxalyl chloride or with a dialkyl oxalate, such as diethyl oxalate, to form the compounds of Formula 1 wherein R is alkyl, preferably ethyl. The ester may be transesterified to any of the other ester moieties or hydrolyzed to metal atom by addition of a base such as sodium hydroxide which is in turn converted to the compound wherein R is hydrogen by the addition of an acid such as hydrochloric acid. The organic acid is in turn converted to the metal or amine salt by the addition of a base such as potassium hydroxide or an amine, respectively.

When using an alkyl oxalyl halide to form the oxamate, the reaction is carried out in a suitable solvent and base. Examples of suitable solvents are dimethylformamide, dioxane, and tetrahydrofuran. Appropriate bases include triethylamine, N-methylmorpholine, dimethylpiperazine and N-methylpiperidine.

When using a dialkyl oxalate, the reaction is run neat or with an additional solvent such as a xylene or diphenylether, if necessary, at a temperature ranging from about 25° C. to the reflux temperature of the system.

Following are illustrative examples of the compounds of the invention. These examples are intended to exemplify the invention, not to narrow the invention.

TABLE 1

R is ethyl

| X | Y |
|---|---|
| 4-Br | H |
| 5-Br | H |
| 6-Br | H |
| 7-Br | H |
| 6-OC$_4$H$_9$ | H |
| 4-Cl | H |
| 5-Cl | H |
| 4-CH$_3$CO | H |
| 6-CH$_3$CO | H |
| 6-Cl | H |
| 7-Cl | H |
| 4-OC$_2$H$_5$ | H |
| 6-OC$_2$H$_5$ | H |
| 6-C$_2$H$_5$ | H |
| 4-F | H |
| 5-F | H |
| 6-F | H |
| 7-F | H |
| 6-O-i-C$_4$H$_9$ | H |
| 6-O-i-C$_3$H$_7$ | H |
| 4-OCH$_3$ | H |
| 5-OCH$_3$ | H |
| 5-C$_3$H$_7$CO | H |
| 6-OCH$_3$ | H |
| 5-CH$_3$ | H |
| 6-CH$_3$ | H |
| 7-CH$_3$ | H |
| 6-NO$_2$ | H |
| 4-OC$_3$H$_7$ | H |
| 5-NH$_2$ | H |
| 5-NHCH$_3$ | H |
| 6-NH$_2$ | H |
| 6-N-di-i-C$_3$H$_7$ | H |
| 6-CO$_2$H | H |
| 6-neo-C$_5$H$_{11}$CO | H |
| 5-CF$_3$ | H |
| 6-CN | H |
| 7-CO$_2$C$_2$H$_5$ | H |
| 4-O-neo-C$_5$H$_{11}$ | H |
| 5-OC$_6$H$_{13}$ | H |
| 6-t-C$_4$H$_9$ | H |
| 7-C$_5$H$_{11}$ | H |
| 7-C$_6$H$_{13}$CO | H |
| 4-Br | 6-Br |
| 4-Cl | 6-Cl |
| 5-Cl | 6-Cl |
| 4-OCH$_3$ | 6-NO$_2$ |
| 4-NO$_2$ | 6-OCH$_3$ |
| 4-CH$_3$ | 6-NO$_2$ |
| 4-Cl | 6-NH$_2$ |
| 6-NH$_2$ | 7-Cl |
| 4-Br | 6-CO$_2$C$_2$H$_5$ |
| 5-Cl | 6-CO$_2$C$_2$H$_5$ |
| 5-Br | 7-Br |
| 4-i-C$_3$H$_7$ | 6-i-C$_3$H$_7$ |
| 5-OC$_2$H$_5$ | 7-OC$_2$H$_5$ |
| 6-C$_4$H$_9$ | 7-C$_4$H$_9$ |
| 4-NO$_2$ | 6-NO$_2$ |
| 5-CN | 7-CN |
| 4-CO$_2$C$_3$H$_7$ | 7-CO$_2$C$_3$H$_7$ |
| 5-CF$_3$ | 7-CF$_3$ |
| 4-NH$_2$ | 6-NH$_2$ |
| 5-Cl | 7-NHC$_2$H$_5$ |
| 5-Br | 7-Cl |
| 4-C$_5$H$_{11}$ | 6-C$_2$H$_5$ |
| 4-OCH$_3$ | 7-O-i-C$_4$H$_9$ |
| 4-CO$_2$CH$_3$ | 6-CO$_2$C$_2$H$_5$ |
| 4-Cl | 6-OC$_2$H$_5$ |
| 5-F | 6-i-C$_3$H$_7$ |
| 6-Br | 7-CN |
| 4-t-C$_4$H$_9$ | 6-CF$_3$ |
| 5-O-neo-C$_5$H$_{11}$ | 7-NH$_2$ |
| 6-NO$_2$ | 7-CO$_2$C$_6$H$_{13}$ |
| 4-C$_2$H$_5$ | 5-Cl |

TABLE 1-continued

[Structure: benzothiazole with positions 4,5,6,7 labeled X at 5, Y at 7, and 2-N-C(=O)-C(=O)-OR substituent with NH]

R is ethyl

| X | Y |
|---|---|
| 5-CF$_3$ | 7-NO$_2$ |
| 4-OCH$_3$ | 7-Cl |

TABLE II

The compounds of Table I are transesterified to compounds wherein R is methyl, propyl, butyl, pentyl, hexyl, heptyl, octyl, isomers thereof, phenyl, benzyl, phenethyl-1 and phenethyl-2.

TABLE III

The compounds of Tables I and II are hydrolyzed to the acid, R is hydrogen, under standard conditions.

TABLE IV

The compounds of Table III are converted to the metal or amine salt, such as sodium, potassium and tris(hydroxymethyl)aminomethane, by standard synthetic pathways.

The following examples are compounds in accordance with this invention.

All temperatures are in degrees centigrade.

EXAMPLE 1

Ethyl (2-Benzothiazolyl)Oxamate

A mixture of 2-aminobenzothiazole (5.0 g., 0.033 mol) and diethyl oxalate (50 ml.) is heated at reflux for 2.5 hours. A white solid precipitates from the cooled reaction mixture. The solid is recrystallized from ethanol (with a hot filtration) to give the desired product (3.72 g., m.p. 185°–186°, 44%).

EXAMPLE 2

Butyl (2-Benzothiazolyl)Oxamate

A mixture of 2-aminobenzothiazole (5.0 g., 0.033 mol), triethylamine (3.5 g., 0.035 mol), butyl oxalyl chloride (5.60 g., 0.034 mol) and anhydrous dimethylformamide (25 ml.) is stirred at room temperature for twenty hours. The reaction mixture is poured into water and the solid precipitate is collected by filtration. The solid is recrystallized from ethanol with a hot filtration to give a yellow solid (2.95 g., m.p. 137°–138°).

EXAMPLE 3

Ethyl (6-Methoxybenzothiazol-2-yl)Oxamate

The 2-amino-6-methoxybenzothiazole (4.5 g., 25 mmol) and ethyl oxalate (25 ml.) are heated under reflux for 1.5 hours during which time a dark brown color develops. Upon cooling a solid (5.86 g.) precipitates. Recrystallization from chloroform-hexane gives yellow crystals of the oxamate (3.4 g., 49%, m.p. 183°–4°.)

The compositions of the present invention are presented for administration to humans and animals in unit dosage forms, such as tablets, capsules, pills, powders, granules, sterile parenteral solutions or suspensions, eye drops, oral solutions or suspensions, and oil in water and water in oil emulsions containing suitable quantities of the compound of Formula 1. The preferred method of administration is orally utilizing an ester of the active compound.

For oral administration, either solid or fluid unit dosage forms can be prepared. For preparing solid compositions such as tablets, the compound of Formula I is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The forms can be dissolved in an aqueous vehicle together with sugar, aromatic flavoring agents and preservatives to form a syrup. An elixir is prepared by using a hydro-alcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The preferred compositions are those adapted for oral administration.

For treatment of allergic conditions of the nose, such as rhinitis, compositions adapted for contact with nasal linings are preferred.

Compositions for inhalation are of three basic types: (1) a powder mixture preferably micropulverized with particle size, preferably from about 1 to about 5 microns; (2) an aqueous solution to be sprayed with a nebulizer; and (3) an aerosol with volatile propellant in a pressurized container.

The powders are quite simply prepared by mixing a compound of Formula I with a solid base which is compatible with lung tissue, preferably lactose. The powders are packaged in a device adapted to emit a measured amount of powder when inhaled through the mouth.

Aqueous solutions are prepared by dissolving the compound of the Formula I in water and adding salt to provide an isotonic solution and buffering to a pH compatible with inhalation. The solutions are dispersed in a spray device or nebulizer and sprayed into the mouth while inhaling.

Aerosols are prepared by dissolving a compound of the Formula I in water or ethanol and mixing with a volatile propellant and placing in a pressurized container having a metering valve to release a predetermined amount of material.

The liquefied propellant employed is one which has a boiling point below 65° F. at atmospheric pressure. For use in compositions intended to produce aerosols for medicinal use, the liquefied propellant should be non-toxic. Among the suitable liquefied propellants which may be employed are the lower alkanes containing up to five carbon atoms, such as butane and pentane, or a lower alkyl chloride, such as methyl, ethyl, or propyl chlorides. Further suitable liquefied propellants are the fluorinated and fluorochlorinated lower alkanes such as are sold under the trademarks "Freon" and "Genetron." Mixtures of the above-mentioned propellants may suitably be employed. Examples of these propellants are dichlorodifluoromethane ("Freon 12"), dichlorotetrafluoroethane ("Freon 114"), trichloromonofluoromethane ("Freon 11"), dichloromonofluoromethane ("Freon 21"), monochlorodifluoromethane ("Freon 22"), trichlorotrifluoroethane ("Freon 113"), difluoromethane ("Genetron 142-A") and monochlorotrifluoromethane ("Freon 13").

The term "unit dosage form," as used in the specification and claims, refers to physically discrete units suitable as unitary dosages for human subjects and animals, each unit containing a predetermined quantity of active material calculated to produce the desired therapeutic diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, coated tablets, powder packets, wafers, granules, cachets, teaspoonfuls, tablespoonfuls, dropperfuls, ampoules, vials, aerosols with metered discharges, segregated multiples of any of the foregoing, and other forms as herein described.

Oral delivery systems with esters of the invention are preferred. Those delivery systems with solid pharmaceutical carriers can be used as an appropriate vehicle. Liquid pharmaceutical carriers can also be used as an appropriate vehicle. These liquid vehicles are separated into aqueous and non-aqueous systems. Oral unit dosage forms which are preferred are tablets, capsules, pills, and powders. Liquid carriers can be divided into a unit dosage by the potential recipient of the drug, for example, droppersful, teaspoonsful, tablespoonsful, and unit dosages of other magnitude.

The ethyl ester is preferred for oral administration for its potency and duration of activity.

An effective but non-toxic quantity of the compound is employed in treatment. The dosage of the compound for treatment depends on the route of administration and the potency of the particular compound. A dosage schedule for humans of from about 0.05 to about 10 mg. of compound in a single dose, administered parenterally or by inhalation in the compositions of this invention are effective for preventing allergy attacks. More specifically, the single dose is from about 0.5 to about 7 mg. of compound. The oral dose is from about 0.5 to about 30 mg. in a single dose. More specifically, the single dose is from about 2 to about 25 mg. of compound. The dosage to be administered can be repeated up to four times daily. However, when it is necessary to repeat treatment, a preferred dosage schedule for some individuals reduces the secondary treatment dosage to from about 0.5 percent to about 20 percent of the above dosages, more specifically, from about 1 to about 10 percent of the above dosages. In this manner, a state of allergy prophylaxis can be maintained. The reduced dosage is taken until that dosage no longer provides effective protection. At that time, the larger dosage is repeated, followed by the reduced dosage. An example of such a dosage schedule is the following: An asthmatic individual swallows 15 mg. of ethyl (2-benzothiazolyl)oxamate. Four hours later, the individual swallows 1 mg. of the same compound and every four to six hours thereafter swallows 1 mg. of the same compound until effective asthma prophylaxis is not provided. The individual then swallows 15 mg. of the same compound, then reduces the oral dosage to 1 mg. four to six hours later. The dosage schedule continues in this manner.

The administration of the compositions of the present invention to humans and animals provides a method for the prophylactic treatment of allergy and anaphylactoid reactions of a reagin or non-reagin, preferably reagin, mediated nature. That is to say, these compositions, when administered to a sensitized individual prior to the time that the individual comes into contact with substances (antigens) to which he is allergic, will prevent the allergic reaction which would otherwise occur. It is believed that the compounds of Formula I function as inhibitors of the release of pharmacological mediators of anaphylaxis following antigen-antibody combination.

For example, the process can be used for treatment of such conditions as bronchial asthma, allergic rhinitis, food allergy, urticaria, exercise or stress induced asthma, anaphylactoid reactions and bird fancier's disease. Preferred conditions for treatment are bronchial asthma, allergic rhinitis, food allergy and urticaria. More preferred conditions are bronchial asthma and allergic rhinitis.

EXAMPLE 4

A lot of 10,000 tablets, each containing 10 mg. of ethyl (2-benzothiazolyl)oxamate is prepared from the following types and amounts of ingredients:

| | |
|---|---|
| Ethyl (2-benzothiazolyl)oxamate | 100 Gm. |
| Dicalcium phosphate | 1,000 Gm. |
| Methylcellulose, U.S.P. (15 cps) | 60 Gm. |
| Talc | 150 Gm. |
| Corn starch | 200 Gm. |
| Magnesium stearate | 10 Gm. |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in preventing hay fever attacked at a dose of one tablet every four to six hours.

EXAMPLE 5

One thousand two-piece hard gelatin capsules, each containing 5 mg. of ethyl (2-benzothiazolyl)oxamate, are prepared from the following types and amounts of ingredients:

| | |
|---|---|
| Ethyl (2-benzothiazolyl)oxamate | 5 Gm. |
| Talc | 150 Gm. |
| Magnesium stearate | 1 Gm. |

The ingredients are mixed well and filled into capsules of the proper size.

Capsules so prepared are useful in preventing attacks of bronchial asthma at a dose of one capsule every four to six hours.

EXAMPLE 6

One thousand tablets, each containing 15 mg. of butyl (2-benzothiazolyl)oxamate are prepared from the following types and amounts of ingredients:

| | |
|---|---|
| Butyl (2-benzothiazolyl)oxamate | 15 Gm. |
| Microcrystalline cellulose NF | 410 Gm. |
| Starch | 100 Gm. |
| Magnesium stearate powder | 3 Gm. |

The ingredients are screened and blended together and pressed into tablets.

The tablets are useful to protect against food allergy at a dose of one tablet before meals.

EXAMPLE 7

One thousand tablets, each containing 20 mg. of ethyl (6-methoxybenzothiazol-2-yl)oxamate are prepared from the following types and amounts of ingredients:

| | |
|---|---|
| Ethyl (6-methoxybenzothiazol-2-yl)oxamate | 20 Gm. |
| Microcrystalline cellulose NF | 410 Gm. |
| Starch | 100 Gm. |
| Magnesium stearate powder | 3 Gm. |

The ingredients are screened and blended together and pressed into tablets.

The tablets are useful to protect against food allergy at a dose of one tablet before meals.

EXAMPLE 8

A sterile preparation suitable for intramuscular injection and containing ethyl (2-benzothiazolyl)oxamate is prepared from the following ingredients:

| | |
|---|---|
| Ethyl (2-benzothiazolyl)oxamate | 2 Gm. |
| Benzyl benzoate | 200 ml. |
| Methylparaben | 1.5 Gm. |
| Propylparaben | 0.5 Gm. |
| Cottonseed oil q.s. | 1,000 ml. |

One milliliter of this sterile preparation is injected for prophylactic treatment of allergic rhinitis.

EXAMPLE 9

An aqueous solution containing 5.0 mg. of the tris(hydroxymethyl)aminomethane salt of (2-benzothiazolyl)oxamic acid per ml. is prepared as follows:

| | |
|---|---|
| Tris(hydroxymethyl)aminomethane salt of (2-benzothiazolyl)oxamic acid | 3 Gm. |
| Sodium chloride | 5 Gm. |
| Water for injection q.s. | 600 ml. |

The THAM salt and sodium chloride are dissolved in sufficient water to make 600 ml. and sterile filtered.

The solution is placed in nebulizers designed to deliver 0.25 ml. of solution per spray.

One spray of the solution is inhaled into the lungs every four to six hours for prevention of asthmatic attack.

EXAMPLE 10

A powder mixture consisting of 0.5 grams of sodium (2-benzothiazolyl) oxamate and sufficient lactose to make five grams of mixture is micropulverized and placed in an insufflator designed to deliver 50 mg. of powder per dose.

The powder is inhaled into the lungs every four to six hours for prevention of asthmatic attacks.

The powder is inhaled intranasally every four hours for prevention of rhinitis.

EXAMPLE 11

In individuals who require continual treatment in the Examples 4–10, the dosage of the Example is given initially and each succeeding administration of the drug is at 1/50 of the initial dosage. This maintenance dosage is continued until effective allergy prophylaxis is not obtained. The initial dosage of Examples 4–10 is then started once more, following by the maintenance dosages.

EXAMPLE 12

After allowing for the different solubilities of the compounds and the activity of the particular compound as measured, for example, by the in vivo rat passive cutaneous anaphylaxis assay, a suitable quantity of each of the compounds, assuming appropriate solubility, of Examples 1-3 and Tables I-IV, is substituted for the active compound in the compositions and uses of Examples 4–10. Results showing anti-allergy activity are obtained.

EXAMPLE 13

The rat passive cutaneous anaphylaxis assay is run in the following manner:

Female Sprague-Dawley 250 Gm. rats are skin-sensitized with rat anti-ovalbumin homocytotropic antibody that is heat labile and has a passive cutaneous anaphylaxis titer of 1:128. After a 72-hour latency period, the animals are challenged i.v. with 4 mg. ovalbumin (OA) + 5 mg. Evans blue dye. The test compound is administered orally in 0.5% methylcellulose in water at an appropriate time internally before iv challenge. Thirty minutes later, the extravascular bluing that results from antigen antibody combination at the skin site is read. Antibody dilutions are used such that in control animals a 4 mm spot is the lowest detectable spot, and 4 or 5 lower dilutions are used to give a range of antibody in each animal. Four to five animals are used for each variable in the experiment. Percent inhibition of the PCA assay is calculated by comparing the spot scores of treated rats with the spot scores of control rats. The spot score is the total number of detectable spots divided by the number of animals.

Ethyl (2-benzothiazolyl)oxamate effectively inhibits the passive cutaneous anaphylaxis reaction when orally administered at a dose of 10 mg./kg. twenty minutes before antigen challenge.

We claim:

1. A compound of the formula

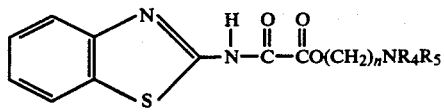

wherein n is 1 or 2, $R_4$ and $R_5$ are the same or different and are alkyl of one to three carbon atoms, inclusive, or a physiologically acceptable acid addition salt thereof.

2. A pharamceutical composition which comprises an antiallergy effective amount of a compound of the formula

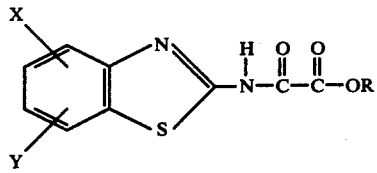

wherein X and Y are the same or different and are hydrogen, fluoro, chloro, bromo, alkyl of one to six carbon atoms, inclusive, alkoxy of one to six carbon atoms, inclusive, nitro, cyano, amino, trifluoromethyl,

wherein $R_1$ is alkyl of one to six carbon atoms, inclusive,

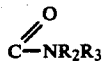

wherein $R_2$ and $R_3$ are the same or different and are hydrogen or alkyl of one to three carbon atoms, inclusive, or $CO_2Q$ wherein Q is alkyl of one to six carbon atoms, inclusive, hydrogen or a physiologically acceptable metal or amine cation with the proviso that at least one of X and Y is other than hydrogen; and R is hydrogen, alkyl of one to eight carbon atoms, inclusive, —$CH_2)_m$ phenyl wherein m is 0, 1 or 2 or $(CH_2)_nNR_4R_5$ wherein n is 1 or 2, and $R_4$ and $R_5$ are the same or different and are alkyl of one to three carbon atoms, inclusive, and a physiologically acceptable metal or amine cation and physiologically acceptable acid addition salts thereof, in association with a pharmaceutical carrier and in the form of a tablet, capsule, aerosol or suspension, said suspension comprising water and a suspending agent.

3. A composition in accordance with claim 2 wherein R is alkyl of one to six carbon atoms or —$CH_2)_m$ phenyl wherein m is 0, 1 or 2.

4. A composition in accordance with claim 3 wherein the composition is suitable for oral means of administration.

5. A composition in accordance with claim 4 wherein the pharmaceutical carrier is a solid.

6. A composition in accordance with claim 4 wherein the pharmaceutical carrier is a liquid.

7. A composition in accordance with claim 6 wherein the liquid is non-aqueous.

8. A composition in accordance with claim 4 wherein the composition is in dosage unit form.

9. A composition in accordance with claim 8 wherein R is alkyl of one to four carbon atoms, inclusive.

10. A composition in accordance with claim 9 wherein X is hydrogen and Y is at the six position.

11. A method for the prophylactic treatment of allergy of a reagin mediated nature which comprises prophylactically administering to a mammal in need of said treatment an anti-reagin mediated allergy effective amount of a compound of the formula

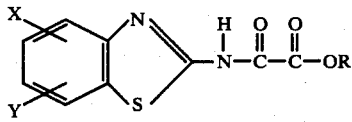

wherein X and Y are the same or different and are hydrogen, fluoro, chloro, bromo, alkyl of one to six carbon atoms, inclusive, alkoxy of one to six carbon atoms, inclusive, nitro, cyano, amino, trifluoromethyl,

wherein $R_1$ is alkyl of one to six carbon atoms, inclusive,

wherein $R_2$ and $R_3$ are the same or different and are hydrogen or alkyl of one to three carbon atoms, inclusive, or $CO_2Q$ where Q is alkyl of one to six carbon atoms, inclusive, hydrogen or a physiologically acceptable metal or amine cation; and R is hydrogen, alkyl of one to eight carbon atoms, inclusive, —$CH_2)_m$ phenyl wherein m is 0, 1 or 2 or $(CH_2)_nNR_4R_5$ wherein n is 1 or 2, and $R_4$ and $R_5$ are the same or different and are alkyl of one to three carbon atoms, inclusive, and a physiologically acceptable metal or amine cation; and physiologically acceptable acid addition salts thereof; in association with a pharmaceutical carrier.

12. A method in accordance with claim 11 wherein the method of administration is oral.

13. A method in accordance with claim 12 wherein the carrier is a solid.

14. A method in accordance with claim 12 wherein the carrier is a liquid.

15. A method in accordance with claim 14 wherein the liqid is non-aqueous.

16. A method in accordance with claim 12 wherein R is alkyl of one to six carbon atoms, inclusive, or —$CH_2)_m$ phenyl wherein m is 0, 1 or 2.

17. A method in accordance with claim 16 wherein X is hydrogen.

18. A method in accordance with claim 17 wherein Y is at the six position.

19. A method in accordance with claim 12 wherein R is alkyl of one to four carbon atoms, inclusive.

20. A method in accordance with claim 19 wherein X is hydrogen.

21. A method in accordance with claim 19 wherein Y is at the six position.

22. A pharmaceutical composition which comprises an antiallergy effective amount of a compound of the formula

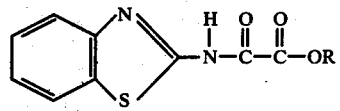

wherein R is hydrogen, alkyl of one to eight carbon atoms, inclusive, —CH$_2$)$_m$ phenyl wherein m is 0, 1 or 2 or (CH$_2$)$_n$NR$_4$R$_5$ wherein n is 1 or 2, and R$_4$ and R$_5$ are the same or different and are alkyl of one to three carbon atoms, inclusive, and a physiologically acceptable metal or amine cation, and physiologically acceptable acid addition salts thereof in association with a pharmaceutical carrier and in the form of a capsule, tablet, or aerosol.

23. A composition in accordance with claim 22 wherein R is ethyl.

24. A composition in accordance with claim 22 wherein R is n-butyl.

25. A composition in accordance with claim 22 wherein R is hydrogen.

* * * * *